United States Patent [19]

Myers

[11] 4,038,173
[45] July 26, 1977

[54] HYDROCRACKING PROCESS USING PLATINUM/ALUMINA CATALYST ACTIVATED AND COOLED WITH HCl

[75] Inventor: John W. Myers, Bartlesville, Okla.

[73] Assignee: Phillips Petroleum Company, Bartlesville, Okla.

[21] Appl. No.: 727,921

[22] Filed: Sept. 29, 1976

Related U.S. Application Data

[60] Continuation-in-part of Ser. No. 664,217, March 5, 1976, Pat. No. 4,003,956, Division of Ser. No. 458,700, April 8, 1974, Pat. No. 3,970,589.

[51] Int. Cl.$^2$ .................... C10G 13/08; B01J 27/06
[52] U.S. Cl. .................................. 208/112; 208/111; 208/217; 252/441; 252/442
[58] Field of Search .......................... 208/112, 111

[56] References Cited

U.S. PATENT DOCUMENTS

| | | | |
|---|---|---|---|
| 3,242,228 | 3/1966 | Riordan et al. | 252/441 X |
| 3,242,229 | 3/1966 | Estes | 208/112 X |
| 3,440,301 | 4/1969 | Lafferty et al. | 252/441 X |
| 3,441,624 | 4/1969 | Myers | 260/667 X |
| 3,449,264 | 6/1969 | Myers | 252/441 |

*Primary Examiner*—Delbert E. Gantz
*Assistant Examiner*—G. E. Schmitkons

[57] ABSTRACT

An improved halogen-activated platinum/alumina catalyst is produced by activating in the presence of a relatively high concentration of HCl treating agent and thereafter slowly cooling in the presence of a relatively low concentration of HCl treating agent.

10 Claims, No Drawings

HYDROCRACKING PROCESS USING PLATINUM/ALUMINA CATALYST ACTIVATED AND COOLED WITH HCl

CROSS-REFERENCE TO RELATED APPLICATION

This is a continuation-in-part of copending application Ser. No 664,217 filed Mar. 5, 1976 (now U.S. Pat. No. 4,003,956), which in turn is a divisional Ser. No. 458,700 filed Apr. 8, 1974, now U.S. Pat. No. 3,970,589.

BACKGROUND OF THE INVENTION

This invention relates to a process of producing improved platinum/alumina catalyst by activating with a hydrogen chloride treating agent.

It is known in the art to utilize halogen treating agents in the activation of active alumina containing catalysts. It has been found, however, that the effectiveness of such treatments can vary widely, and in particular can be decreased when the cooling time for the activated catalyst is relatively long as is generally the case in a commercial operation.

SUMMARY OF THE INVENTION

It is an object of this invention to provide a hydrocarbon conversion catalyst of improved activity; it is a further object of this invention to provide a process for hydrogen chloride activating a platinum/alumina catalyst which is applicable to commercial scale operations; it is yet a further object of this invention to provide a process for hydrogen chloride activation of a platinum/alumina catalyst wherein the cooling time after activation is relatively long; and it is still yet a further object of this invention to achieve improved isomerization conversions.

In accordance with this invention, a platinum/alumina catalyst is produced by activating in the presence of a relatively high concentration of hydrogen chloride and thereafter slowly cooled in the presence of a relatively low concentration of hydrogen chloride.

DESCRIPTION OF THE PREFERRED EMBODIMENT

Myers, U.S. Pat. No. 3,449,264, issued June 10, 1969, broadly discloses halogen activation of active alumina catalysts, the invention herein being an improvement over the basic invention of said Myers patent.

The active platinum/alumina catalysts which are prepared in accordance with this invention are basically platinum supported on an active alumina base. These catalysts are well known in the prior art. They contain from 0.01 to 10, preferably 0.1 to 1, weight percent platinum based on total catalyst weight on the alumina base. These catalysts can also contain a minor amount of halogen incorporated during preparation of the catalyst, chlorine and/or fluorine being the two halogens commonly present. Although one or both of these halogens can be present in the catalyst prior to activation by the process of the present invention, the catalyst containing them is not the equivalent of the catalyst which has been activated by the present process. The amount of halogen in the catalyst as prepared (i.e. prior to activation in accordance with this invention), if any, is usually less than about 1.5 weight percent of the catalyst.

To produce these catalysts, an alumina, well known in the art as an "active" alumina, is essential. Active aluminas may be synthetically prepared as by calcination of alumina gels which are formed by adding such reagents as ammonium hydroxide to a salt of aluminum, such as aluminum chloride or aluminum nitrate. These aluminas are generally gamma or eta aluminas depending upon the dehydrating conditions used. Similar active aluminas may be prepared by calcination of naturally occurring aluminas such as the monohydrate and the trihydrate. Bauxite is a common source of active alumina when properly calcined and dehydrated. The alumina base of the catalyst may contain minor amounts of silica and boron oxide. The amounts of these materials should be less than about 30 weight percent, and preferably less than about 10 weight percent of the catalyst base components to produce the most active catalysts.

The alumina supported platinum catalysts are first activated with anhydrous HCl and thereafter cooled while in contact with anhydrous HCl.

During the activation step the platinum metal-alumina or platinum metal-halogen-alumina catalyst is heated in the presence of the treating agent at a temperature of 600°–1500° F, for a period of at least 0.1 hours and up to 100 hours or more, preferably one-half to six hours. Suitable conditions are one-half to four hours at 900°–1500° F without the HCl followed by ½ to 4 hours at 900°–1500° F in contact with the HCl. The treating agent may be carried in a dry carrier gas. If a carrier gas is used, the treating agent concentration is preferably at least about 30 volume percent and more preferably over about 60 volume percent HCl based on the total volume of HCl gas and carrier gas; thus 30–100 percent hydrogen chloride is suitable, 40–75 percent being generally preferred.

Generally the cooling time will be at least 0.5 hours, preferably 0.6 to 10 hours. The volume percent of hydrogen chloride gas during the cooling step must be within the range of 1 to 20, preferably 2 to 16, more preferably 2 to 6 volume percent based on the total volume of HCl gas and carrier gas. The carrier gas can be hydrogen, nitrogen, methane, ethane, or any other gas essentially inert in the treating process, or mixtures of such gases. A mixture of hydrogen and nitrogen is preferred, the mixture preferably containing 5 to 50 weight percent hydrogen. The cooling time referred to is the time to cool from the activation temperature of 900°–1500° F to about 200° F to 400° F. Below 400 the presence or absence of HCl has little effect on the catalyst; below 200° F it has no effect. Thus once the temperature reaches 200°–400° F there is nothing critical about the way it is treated so long as it is not subjected to obvious poisons such as water.

The carrier gas can be hydrogen, nitrogen, methane, ethane or any other gas essentially inert in the treating process or mixtures of such gases. Preferably the carrier gas in the activation step is hydrogen, and in the cooling step the carrier gas is preferably either hydrogen or a mixture of hydrogen and nitrogen.

Preferably the catalyst is activated at pressures somewhat higher than atmospheric, i.e., 10 psig. In most instances the pressure will be within the range of 0–25 psig.

The catalysts of the present invention are particularly applicable to the isomerization of isomerizable hydrocarbons including acyclic paraffins, and naphthenes. These catalysts are particularly suitable for the isomerization of straight chain paraffins containing four to eight carbon atoms per molecule including n-butane, n-pentane, n-heptane, and the like. Some examples of naphthenes which can be isomerized with these catalysts are methylcyclopentane, dimethylcyclopentane, cyclohexane, methylcyclohexane, and the like. Actually these are equilibrium reactions as follows:

cyclohexane ⇌ methycyclopentane
methylcyclohexane ⇌ dimethylcyclopentane
pentane ⇌ methylbutane
n-hexane ⇌ methylpentanes ⇌ dimethylbutanes Conditions can be adjusted to give hydrocracking, as for instance to produce butane from n-octane. Preferred process conditions for hydrocracking are as follows. Pressure: 50-5000 psig, preferably 100-3000 psig; temperature: 200°-800° F, preferably 300°-700° F; liquid hourly space velocity: 0.1-30, preferably 0.5-20; and hydrogen/hydrocarbon mole ratio: 0.5-30, preferably 2-20. Applicable feeds include $C_5$ and higher boiling hydrocarbons such as naphthas and distillates. The catalyst is especially useful in hydrocracking to produce $C_4$ and lighter hydrocarbons. Feeds should be substantially free of poisons such as water, oxygen-containing organic compounds and sulfur compounds.

The isomerization condition and recovery procedures can be varied to achieve the desired conversion in a manner known in the art. Most preferred is normal butane which is isomerized to isobutane.

Hydrocarbons to be isomerized are contacted with the activated catalysts prepared in accordance with the invention at an isomerization temperature of about 100°-600° F, more preferably 150°-450° F, in the presence of free hydrogen. The hydrogen-hydrocarbon mol ratios normally used during isomerization are within the range of about 0.25 to 10 to insure long catalyst life. Liquid hourly space velocities, i.e., the volume of liquid charge per hour per volume of catalyst, of about 0.1 to 15 are satisfactory and pressures within the range of atmospheric to 1500 psig in the isomerization zone are suitable.

Maintenance of catalyst activity during the isomerization process is aided by the inclusion of 0.001 to about 1 weight percent chloride in the feed in the form of chlorinated hydrocarbon promoters such as carbon tetrachloride, chloroform, ethyl chloride, isopropyl chloride, etc. This is not a substitute for the activation of the catalyst but it aids in maintaining over long process periods the high level of catalyst activity produced by the invention catalysts.

The isomerization process can be carried out either batchwise or continuous, preferably the latter. In a continuous process it is to be understood that hydrogen in the effluent product can be separated and recycled and that recycling of isomerization promoters, if employed, can be practiced.

EXAMPLE I

The activity of the catalysts prepared in accordance with the invention was tested by isomerizing n-butane at about 150° F. The data are shown in Table 1.

Table 1

| Run number: | 1 | 2 | 3 | invention 4 | 5 | 6 | 7 | invention 8 | 9 |
|---|---|---|---|---|---|---|---|---|---|
| Activating gas,[1] l/hr. | 15 | 15 | 15 | 15 | 14.7 | 14.7 | 15 | 15 | 15 |
| HCl, volume % | 56 | 56 | 56 | 56 | 58 | 58 | 56 | 56 | 56 |
| $H_2$, volume % | 44 | 44 | 44 | 44 | 42 | 42 | 44 | 44 | 44 |
| Activating temp., ° F | 1200 | 1200 | 1200 | 1200 | 1200 | 1200 | 1200 | 1200 | 1200 |
| Activating pressure, psig | atm. | atm. | atm. | atm. | atm. | atm. | 10 | 10 | atm. |
| Activating time, hrs. | 1.5 | 1.5 | 2.1 | 2.0 | 1.5 | 1.5 | 2.0 | 2.0 | 2.0 |
| Cooling gas flow, l/hr. | 15 | 6.5 | 15 | 95 | 14.7 | 14.7 | 15 | 55 | 47 |
| HCl, volume % | 56 | — | 56 | 8.9 | 58 | 58 | 56 | 15 | 18 |
| $H_2$, volume % | 44 | 100 | 44 | 6.8 | 42 | 42 | 44 | 12 | 14 |
| $N_2$, volume % | — | — | — | 84.3 | — | — | — | 73 | 68 |
| Cooling Time,[2] hrs. | 0.2[3] | 0.2 | 0.2 | 0.6 | 0.4[3] | 3[3] | 0.2 | 1.2 | 0.2 |
| Isobutene produced, weight %[4] total effluent | 65.8 | 57.2 | 71.4[5] | 70.9[5] | 61.8[5] | 55.5[5] | 73.3[5] | 74.0[5] | 71.0[5] |
| Catalyst weight, grams | 20 | 20 | 17.2 | 17.2 | 20 | 20 | 17.2 | 17.2 | 17.2 |
| Catalyst support | eta alumina | eta alumina | gamma alumina | gamma alumina | eta alumina | eta alumina | gamma alumina | gamma alumina | gamma alumina |
| Platinum, weight % | 0.5 | 0.5 | 0.4 | 0.4 | 0.3 | 0.3 | 0.4 | 0.4 | 0.1 |

[1]Catalyst heated in $H_2$ at 1000-2000° F. before activation.
[2]Cooling time to about 200° F.
[3]Cooling time to about 400° F
[4]Isometrization conditions 150° F, atmospheric pressure, 0.2 LHSV of n-butane, no $H_2$ used.
[5]Before testing, the catalyst was purged for 1 hour with hydrogen at 400° F.

Inspection of the data presented in Table 1 shows that it is necessary to have HCl in the ambient while cooling newly activated hot catalyst or the isomerization activity of the catalyst is substantially diminished as a comparison between Run 1 (65.8 mole percent isobutane formed, HCl in cooling ambient) and Run 2 (57.2 mole percent isobutane formed, no HCl in cooling ambient) demonstrates. Neither runs 1 or 2 is within the scope of the invention since the cooling times in both are short and thus the invention is not needed. Run 6, compared with Run 5, shows that relatively long cooling times, i.e., 3 hours, for lowering the temperature of the hot catalyst is detrimental even in the presence of HCl when the HCl in the cooling ambient is the same as in the activating gas. Run 6 is outside the scope of the invention for this reason; Run 5 is outside the scope of the invention because the cooling time is short. The procedure is satisfactory only when short cooling periods, i.e., 0.4 hours or less, are utilized as Runs 1 and 5 show. When long cooling times (0.5 hour or more ) are used such as can be expected in commercial production of chloride-activated platinum/alumina catalyst, it is necessary to reduce the HCl concentration in the cooling ambient to about 15 percent or less if an active isomerization catalyst is to result. Inventions Runs 4 and 8 clearly demonstrate this (compare for instance Run 8 with controls 5 and 6). Run 8 also shows that it may be desirable to activate the catalyst under a slight pressure rather than at atmospheric pressure since the catalyst activity appears somewhat improved by so doing. cl

EXAMPLE II

Another series of activation tests was carried out using 10 or 25 psig in the activating chamber in which the compositions of the activating gas and cooling gas were investigated as to their effects upon the isomerization activity of the catalysts. During the cooling period the pressure was reduced to atmospheric, the gas flows were altered, if desired, and nitrogen was added, if desired. The catalysts were tested using isomerization conditions similar to those encountered in commerical processes. The results are presented in Table 2.

medium even when practicing prolonged cooling of the activated catalysts providing the concentration of HCl in the cooling medium is low (about 4 volume percent in these runs). Two volume percent HCl thus gives satisfactory results and 4 volume percent is somewhat better based on the isomerization results.

Thus the invention discloses a method of cooling freshly made, suitably HCl-activated isomerization catalysts so that activity of the catalysts is maintained even though long cooling periods are employed. The pressure of the activating medium, commonly a HCl-H$_2$ mixture, can range from about atmospheric pressure to Table 2

| | Effect of Catalyst Activation Conditions on n-Butane Isomerization | | | | | | | | | | | |
|---|---|---|---|---|---|---|---|---|---|---|---|---|
| | | | | | Invention | | | | Invention | | | |
| Run number: | 10 | 11 | 12 | 13 | 14 | 15 | 16 | 17 | 18 | 19 | 20 | 21 | 22 |
| Activating gas[1] | | | | | | | | | | | | | |
| HCl, volume % | 15 | 30 | 62 | 62,17 | 62,17 | 62 | 41 | 41 | 41 | 62 | 62 | 62 | 62 |
| H$_2$, volume % | 85 | 70 | 38 | 38,83 | 38,83 | 38 | 59 | 59 | 59 | 38 | 38 | 38 | 38 |
| Activating temp., °F[2] | 1250 | 1250 | 1250 | 1250 | 1250 | 1250 | 1250 | 1250 | 1250 | 1250 | 1250 | 1250 | 1250 |
| Activating pressure, psig | 25 | 25 | 25 | 10 | 10 | 10 | 10 | 10 | 10 | 25 | 25 | 25 | 10 |
| Activating time, hrs. | 2 | 2 | 2 | 11 | 11 | 2 | 2 | 2 | 2 | 2 | 2 | 2 | 2 |
| Cooling gas flow, l/hrs. | 29 | 29 | 29 | 29 | 114 | 29 | 29 | 114 | 114 | 109 | 109 | 114 | 114 |
| HCl, volume % | 15 | 30 | 62 | 17 | 4 | 62 | 41 | 4 | 2 | 16 | 16 | 4 | 4 |
| H$_2$, volume % | 85 | 70 | 38 | 83 | 10 | 38 | 59 | 10 | 2 | 11 | 11 | 10 | 10 |
| N$_2$, volume % | — | — | — | — | 86 | — | — | 86 | 96 | 73 | 73 | 86 | 86 |
| Cooling time, hrs. to ≈200° F. | 0.2 | 0.2 | 0.2 | 0.2 | 3.1 | 0.2 | 0.2 | 3.7 | 3.3 | 2.9 | 3.7 | 3.6 | 4.7 |
| Isobutane produced, wt. % in C$_4$ effluent[3] | 48 | 58 | 60.5 | 59 | 55 | 60 | 56 | 59 | 57 | 57 | 55 | 60 | 60.5 |

[1]Total activating gas flow of 29 l/hour, 34.6 g. catalyst treated, catalyst contains 0.4 wt. % platinum-impregnated on gamma alumina of ~218 m$^2$/g surface area.
[2]Catalyst heated about 2 hours in H$_2$ at 1250 before starting activation.
[3]Isomerization conditions: 325° F, 500 psig, 0.5 H$_2$/butane mole ratio, 4 n-butane LHSV.

Inspection of the data presented in Table 2 reveals that the concentration of HCl in the HCl-H$_2$ activating gas ambient is preferably greater than 30 volume percent and is more preferably at least about 60 volume percent to obtain active catalysts as Runs 11, 12, 15 and 16 show. Good results are obtained when the pressure of the activating ambient is either 10 or 25 psig as Runs 12 and 15 show, providing the activated catalysts are quickly cooled in the rich HCl-containing activating ambient. Run 13 shows that it is possible to reduce the HCl concentration from 62 volume percent to 17 volume percent during the last half of the activating process and still obtain an active catalyst providing that the catalyst is quickly cooled, i.e., about 0.2 hour, in the less rich HCl-containing activating ambient. Invention Run 14 shows when a longer cooling period, i.e., about 3 hours, is used coupled with lowering the HCl concentration in the cooling ambient to 4 volume percent, the activity of the catalyst is diminished somewhat but it is still relatively active as the isomerization results reveal. Invention runs 19 and 20 show that even using suitably HCl activated catalysts, long cooling periods, i.e., about 3-4 hours, to lower the catalyst temperature to about 200° F decrease catalyst activity somewhat even when the concentration of HCl in the cooling ambient is about 16 volume percent, the longer the cooling period the greater the decrease. (Note that Run 13 in which 17 volume percent HCl is used in the cooling ambient produces an active catalyst when a short cooling period is employed.) Comparison of Run 16 with invention run 18 shows that slow cooling of properly activated catalyst in an ambient containing a low percent HCl (i.e., in accordance with the invention) can actually give improved isomerization activity of the catalyst compared with quickly cooled catalyst (Run 16) which would otherwise be expected to give better results. Invention runs 17, 21 and 22 show that active catalysts can be obtained using suitable amounts of HCl in the activating somewhat above. Good results were obtained at pressures ranging from 0 to 25 psig in actual tests. It is essential to have a comparatively low concentration of HCl present ambient during prolonged cooling periods.

EXAMPLE III

Gamma alumina extrudate (1.4 mm in diameter) impregnated with an aqueous solution of chloroplatinic acid and hydrochloric acid to add 0.35 wt. % Pt and 1.0 wt. % HCl, was dried at about 140° F and calcined at about 800° F. A portion of this calcined material was heated for 2 hours at about 1340° F in a N$_2$-H$_2$ mixture containing 5 mole % H$_2$ and then for an additional 2 hours at about 1340° F in a H$_2$-HCl mixture containing 63 mole % HCl. The catalyst was then cooled to about 200° F in 3.7 hours in a gas mixture having the mole % composition HCl-5, H$_2$-5, and N$_2$-90.

The hydrocracking activity of this catalyst was demonstrated with n-butane feed. Normal butane containing 100–200 ppm chloride (as CCl$_4$) was passed over a portion of the catalyst at 345° F and 380° F, 500 psig, and a H$_2$/butane mole ratio of 0.55 with the liquid hourly space velocity adjusted to vary conversion. At 345° F, only about 1.4 wt. % of the butane was hydrocracked to lighter hydrocarbons when the butane product contained 59% isobutane. However, at 380° F about 6.2% of the butane was hydrocracked to lighter hydrocarbons when the butane product contained 59% isobutane. This increase in hydrocracking of the relatively stable butane molecule by a factor of over 4 when the temperature was raised from 345° F to the low temperature of 380° F demonstrates the high hydrocracking activity of this catalyst when reaction severity is increased. Hydrocracking is generally applied to hydrocarbons heavier than butane such as naphthas and distillates. Since these heavier hydrocarbons are normally much easier to hydrocrack than butane, this substantial hydrocracking of butane illustrates the high hydrocracking potential of this catalyst.

While this invention has been described in detail for the purpose of illustration, it is not to be construed as limited thereby but is intended to cover all changes and modifications within the spirit and scope thereof.

I claim:

1. A hydrocarbon conversion process which comprises contacting a hydrocarbon under hydrocracking conditions with an active alumina supported platinum catalyst prepared by contacting said catalyst at a temperature within the range of 600°–1500° F with a dry activating gas comprising 30 to 100 volume percent anhydrous hydrogen chloride for at least 0.1 hour; and thereafter cooling the thus-activated catalyst for a time of at least 0.5 hour in the presence of a dry carrier gas containing 1 to 20 volume percent anhydrous hydrogen chloride.

2. A process according to claim 1 wherein said feed is a $C_5$ or higher boiling hydrocarbon.

3. A process according to claim 1 wherein said feed in n-octane and wherein said n-octane is converted to butane.

4. A process according to claim 1 wherein said hydrocracking conditions are: pressure, 100–3000 psig; temperature: 300–700° F; liquid hourly space velocity, 0.5–20 and $H_2$/hydrocarbon mole ratio, 2–20.

5. A method according to claim 4 wherein said alumina is one of $\gamma$ alumina or $\eta$ alumina and said hydrogen chloride is present in said carrier gas in an amount within the range of 2 to 6 volume percent.

6. A method according to claim 4 wherein said alumina is $\gamma$ alumina.

7. A method according to claim 1 wherein said HCl is present in an amount within the range of 40 to 75 volume percent during said activation step and said contacting is carried out for a time within the range of 0.5 to 6 hours and said cooling is carried out over a time within the range of 0.5 to 10 hours.

8. A method according to claim 4 wherein said activation temperature is within the range of 1050° to 1400° F.

9. A method according to claim 8 wherein said alumina is $\gamma$ alumina, a concentration of said hydrogen chloride in said activation step is 41 to 62 volume percent, and a concentration of hydrogen chloride during said cooling step is 2 to 6 volume percent.

10. A method according to claim 9 wherein hydrogen is present as a carrier gas in said activation step and said carrier gas for said cooling is a mixture of hydrogen and nitrogen.

* * * * *